United States Patent [19]

Hartman et al.

[11] Patent Number: 5,490,972
[45] Date of Patent: Feb. 13, 1996

[54] RAISING MECHANISM FOR INCUBATOR COVER

[75] Inventors: Gary S. Hartman, Spencerport; James G. Miller, Hilton, both of N.Y.

[73] Assignee: Johnson & Johnson Clinical Diagnostics, Inc., Rochester, N.Y.

[21] Appl. No.: 236,909

[22] Filed: Apr. 29, 1994

[51] Int. Cl.[6] .................................................. G01N 37/00
[52] U.S. Cl. .............................. 422/64; 422/63; 422/103; 422/104; 436/43; 436/46; 436/48; 435/809
[58] Field of Search .............................. 422/63, 64, 103, 422/104; 435/809; 436/43, 48, 46

[56] References Cited

U.S. PATENT DOCUMENTS

| | | | |
|---|---|---|---|
| 4,257,862 | 3/1981 | Schinipelsky et al. | 204/195 R |
| 4,512,952 | 4/1985 | Blanding et al. | 422/63 |
| 4,798,705 | 1/1989 | Jakubowicz et al. | 422/63 |
| 4,963,333 | 10/1990 | Shaw et al. | 422/99 |
| 5,034,191 | 7/1991 | Porte | 422/64 |
| 5,037,613 | 8/1991 | Shaw et al. | 422/64 |
| 5,192,502 | 3/1993 | Kureshy et al. | 422/64 |

FOREIGN PATENT DOCUMENTS 60-57259  4/1985  Japan.

Primary Examiner—James C. Housel
Assistant Examiner—Long V. Le
Attorney, Agent, or Firm—Dana M. Schmidt

[57] ABSTRACT

An incubator and its cover are provided for an analyzer, and especially a mechanism for raising and lowering the cover. Such a mechanism includes a connector between the cover and incubator that allows the cover to be raised to a superimposed position, but not rotated. A pivot pin is mounted directly between the connector and the cover so that the cover can be pivoted relative to the connector to complete exposure of the incubator for access. A latch is provided on the connector for automatically latching the cover in the raised position as soon as the cover is pivoted in the plane at least part way from the superimposed position.

7 Claims, 9 Drawing Sheets

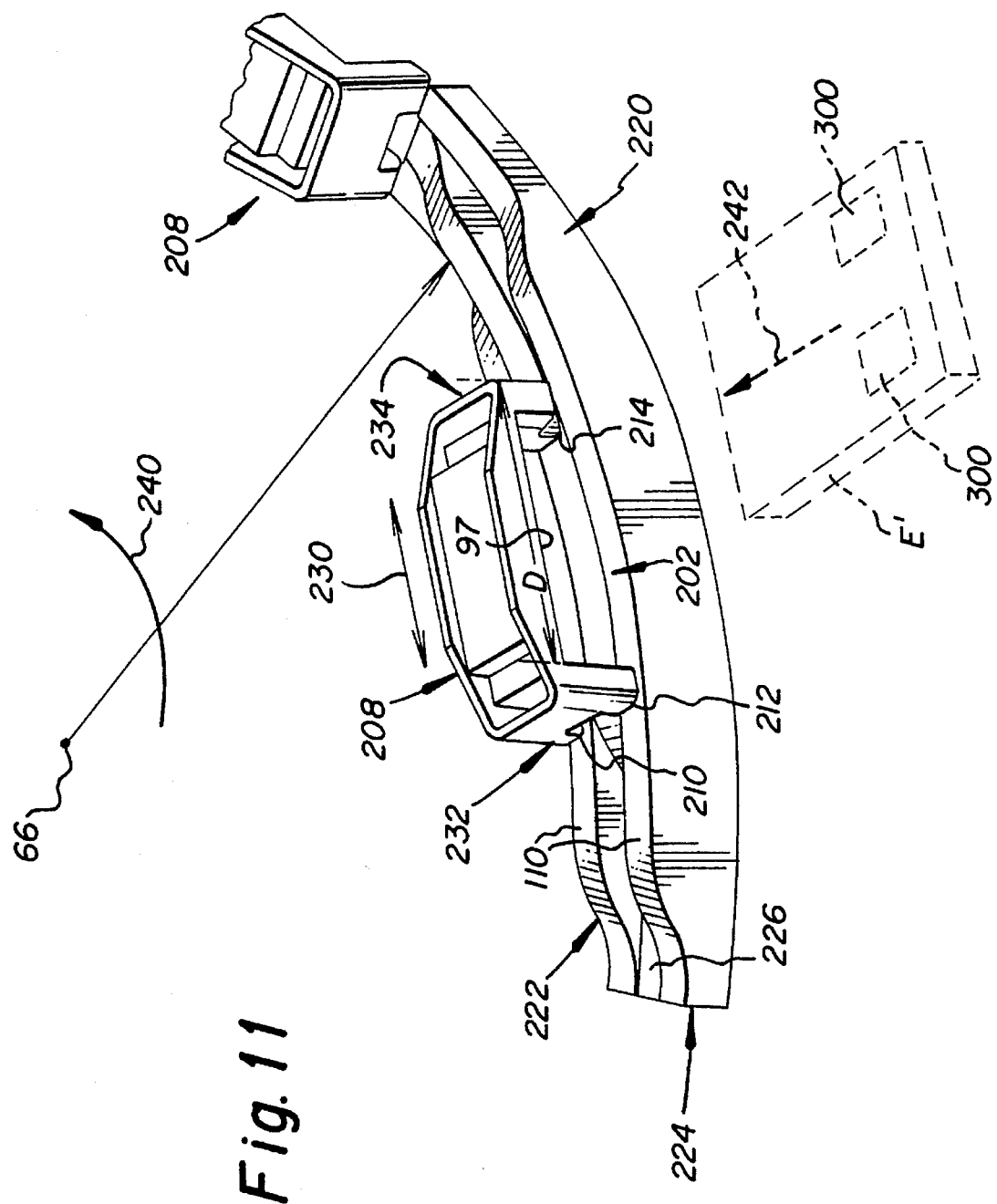

5,490,972

1

RAISING MECHANISM FOR INCUBATOR COVER

FIELD OF THE INVENTION

This invention relates to an incubator and its cover, for use in an analyzer, and a mechanism for raising and lowering the cover.

BACKGROUND OF THE INVENTION

Incubators in clinical analyzers comprise, typically, a rotor having stations around the periphery for holding slide test elements, as shown in U.S. Pat. No. 4,963,333, and a cover over the rotor. The cover is removable for cleaning the rotor and/or for removing slide jams on the rare occasion that they occur.

Various mechanisms have been provided for making such cover removable. In those instances in which the cover is a light-weight piece of plastic, the problem and solution are trivial—a screw can be removed from the center axis and the cover lifted off. Or, the cover is unsnapped and lifted like a clam shell along a horizontal pivot. However, in some instances those trivial mechanisms are not acceptable. For example, if it is essential that the cover be only minimally disturbed, and/or that it not be actually physically removed from the incubation site, these are insufficient. Particularly those are insufficient if the cover for the incubator is itself part of a second incubator disposed above the incubator being covered. In such a case, the cover that is also an incubator cannot be tipped out of the horizontal plane, nor can it be disconnected from the site due to electrical connections and the like. Furthermore, by being itself an incubator or part of an incubator, the cover now has substantial weight which makes lifting it away or back in place a more problematic exercise, particularly since the slide elements within the cover incubator will not tolerate jarring as would occur if the cover should inadvertently fall onto the lower incubator.

Hence, prior to this invention there has been a need for a mechanism that will raise and lower an incubator cover that is sensitive to disturbance and/or tipping, in a convenient and safe manner, particularly when the cover is itself part of another incubator.

RELATED APPLICATIONS

The concept of mounting a second incubator in position above and covering a first incubator is disclosed and claimed in commonly-owned and co-filed U.S. application Ser. No. 235,041 entitled Twin Rotor Incubator Assembly, by James Miller.

SUMMARY OF THE INVENTION

The above problems have been solved by a mounting mechanism for the cover which allows the cover to be first raised, and then pivoted away from the normal position it has superimposed over the incubator under it.

More specifically, in accord with one aspect of the invention, there is provided an incubator useful in a clinical analyzer, the incubator comprising a rotor having stations thereon for receiving a test element, means for rotating the rotor about an axis, a cover for the incubator, and mounting means permitting movement of the cover from a covering position to an access position moved away from the incubator to allow operator access to the incubator. The incubator is improved in that the mounting means comprise a connector on which the cover is mounted, between the cover and the incubator, constructed to permit the cover to be raised from and lowered to the covering position to a raised, superimposed position, but not to be pivoted, a pivot pin on the connector for pivoting the cover within a horizontal plane from the raised, superimposed position to a raised, incubator-accessible position, and back, and latch means on the connector for automatically latching the cover in the raised position as soon as the cover is pivoted in the plane a predetermined angle away from the superimposed position.

In accord with another aspect of the invention there is provided in such an incubator, an improvement in which the mounting means comprise a latch, and means for automatically engaging and disengaging the latch when the cover is moved at least part way out of the covering position, the latch being disposed when engaged to keep the cover from returning to the covering position.

Accordingly, it is an advantageous feature of the invention that an incubator cover can be moved from its covering position to an incubator-accessible position without tilting the cover out of a horizontal plane and without completely disconnecting it from the incubation site.

It is another advantageous feature of the invention that such a cover can be moved to an incubator-accessible position safely and easily even when the cover has substantial weight, as for example when it is part of another incubator.

It is a related advantageous feature of the invention that such a cover automatically retains itself in a raised position once it starts to move to its final incubator-accessible position, thus freeing up the operator to do other things besides holding the cover up.

Other advantageous features will become apparent upon reference to the Detailed Description, when read in light of the attached drawings.

BRIEF DESCRIPTION OF THE DRAWINGS

FIG. 11 is a fragmentary isometric view of portions of the upper incubator carried by cover 80.

DETAILED DESCRIPTION OF PREFERRED EMBODIMENTS

The description which follows is of the preferred embodiments, in which the incubator being covered is for colorimetric-type slide test elements of a preferred type and in which the cover supports a second incubator which is for potentiometric-type slide test elements of a particular type. In addition, this invention is useful regardless of which kind or design of slide test elements is processed in the incubator being covered, or the kind or design of test elements incubated in the incubator carried by the cover, or indeed whether or not a second incubator is carried by the cover. It is also useful regardless of the mechanism for loading slide test elements into one or both incubators.

Figure 1:
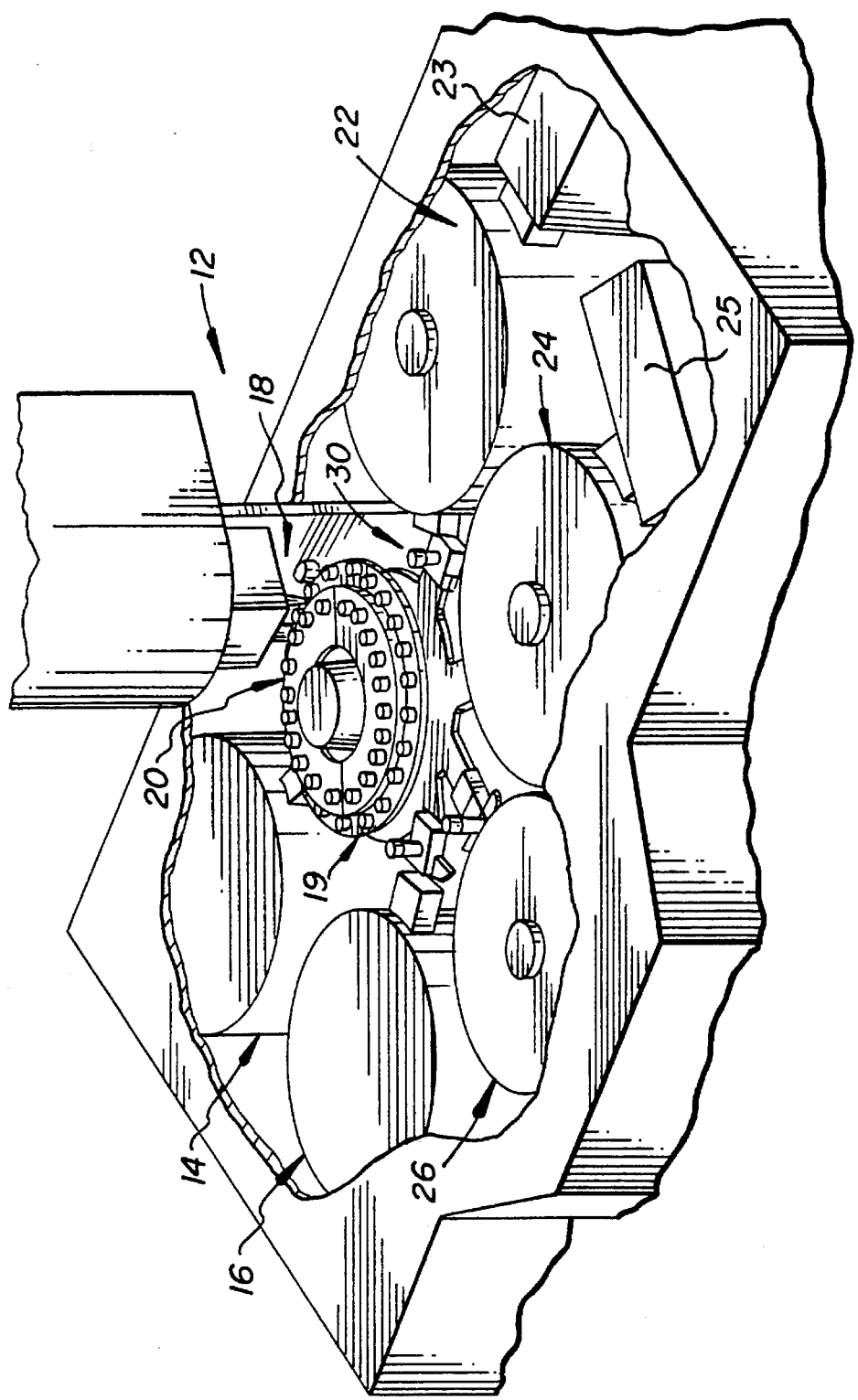
FIG. 1 is a fragmentary isometric view of an analyzer constructed with the incubator of this invention.

As shown in FIG. 1, it is conventional for an analyzer 12 to have one or more supplies of slide test elements at stations 14 and 16, a supply of patient samples 19 and of disposable tips 21 at a rotating station 20, an aspirating and dispensing tower 18 adjacent station 20, a distributor arm 30 under station 20 to receive slide test elements to move them to tower 18 and to various incubators, at least three incubators 22, 24 and 26 for incubating slide elements received from distributor 30, and readers 23 and 25 of incubated slide elements optionally disposed to one side of the incubators, all as described in, e.g., U.S. Pat. No. 4,512,952.

In this invention, as described in the aforesaid related application Ser. No. 235,041, incubator 26 is replaced with a pair of stacked incubators 36 and 200 more clearly shown in FIG. 2, the upper incubator 200 being carried by cover 80 for lower incubator 36. (The cover for the upper incubator is not shown.)

Figure 2:
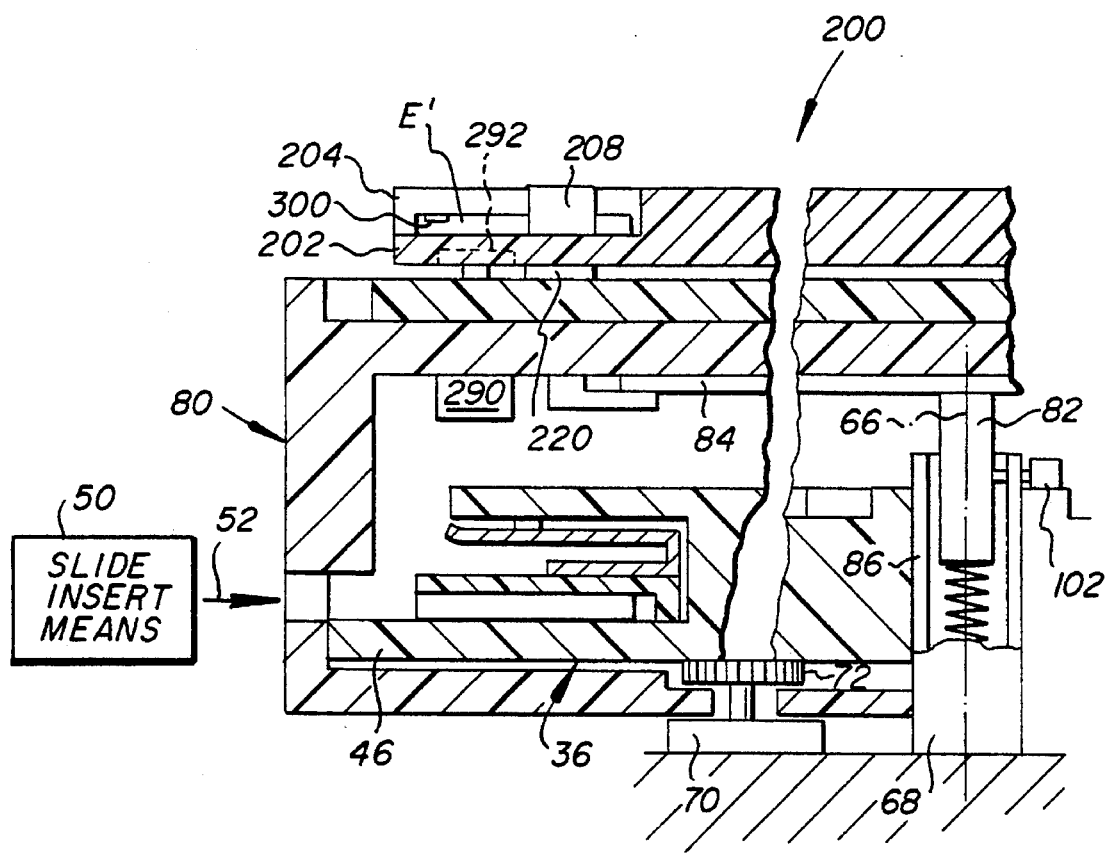
FIG. 2 is a fragmentary, partially schematic, elevational view partially in section, of the incubator and cover of the invention, showing the relationship of the incubator with respect to other parts of the analyzer.
Figure 3:
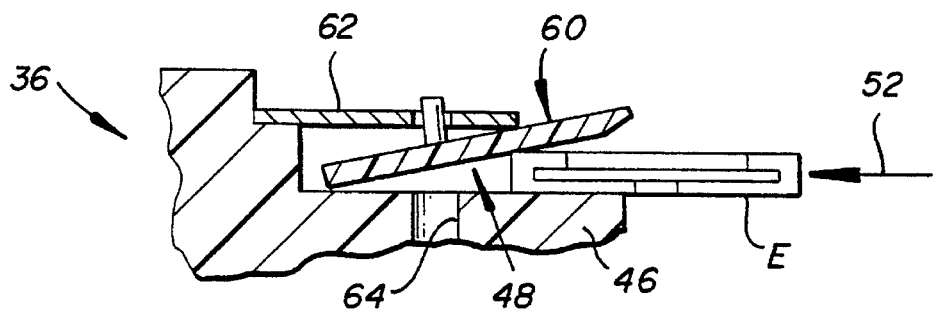
FIG. 3 is a fragmentary elevational view in section showing details of the lower incubator stations (from a direction opposite to that shown in FIG. 2)

Referring first to lower incubator 36, FIGS. 2 and 3, that is preferably for colorimetric-type test elements of the type available from Eastman Kodak Company under the trademark "Ektachem". Such elements produce a detectable color change. Incubator 36 is conventional, and is preferably dedicated to rate-type assays. It comprises, as shown in U.S. Pat. No. 5,106,586, a rotor 46 that receives at stations 48, FIG. 3, a slide test element E from any slide insert means 50, FIG. 2, that moves the slide in the direction of arrow 52. An evaporation cap 60 is spring-biased by spring 62, down onto the slide element. Spring 62 can be flat, as shown, or a J-spring as in the '586 patent. The element E can be read by a reader (not shown) located below rotor 46 that illuminates element E through aperture 64. Rotor 46 is rotated in turn about axis 66 because it is mounted by bearings (not shown). Any conventional motor 70 can rotate rotor 46, using, for example, a drive pinion 72.

To obtain access to incubator 36, cover 80 of that incubator has to be moved out of the way.. For reasons that will be readily apparent, this needs to be done while maintaining cover 80 in a horizontal plane and without disconnecting it from the site of the two incubators.

Figure 4:
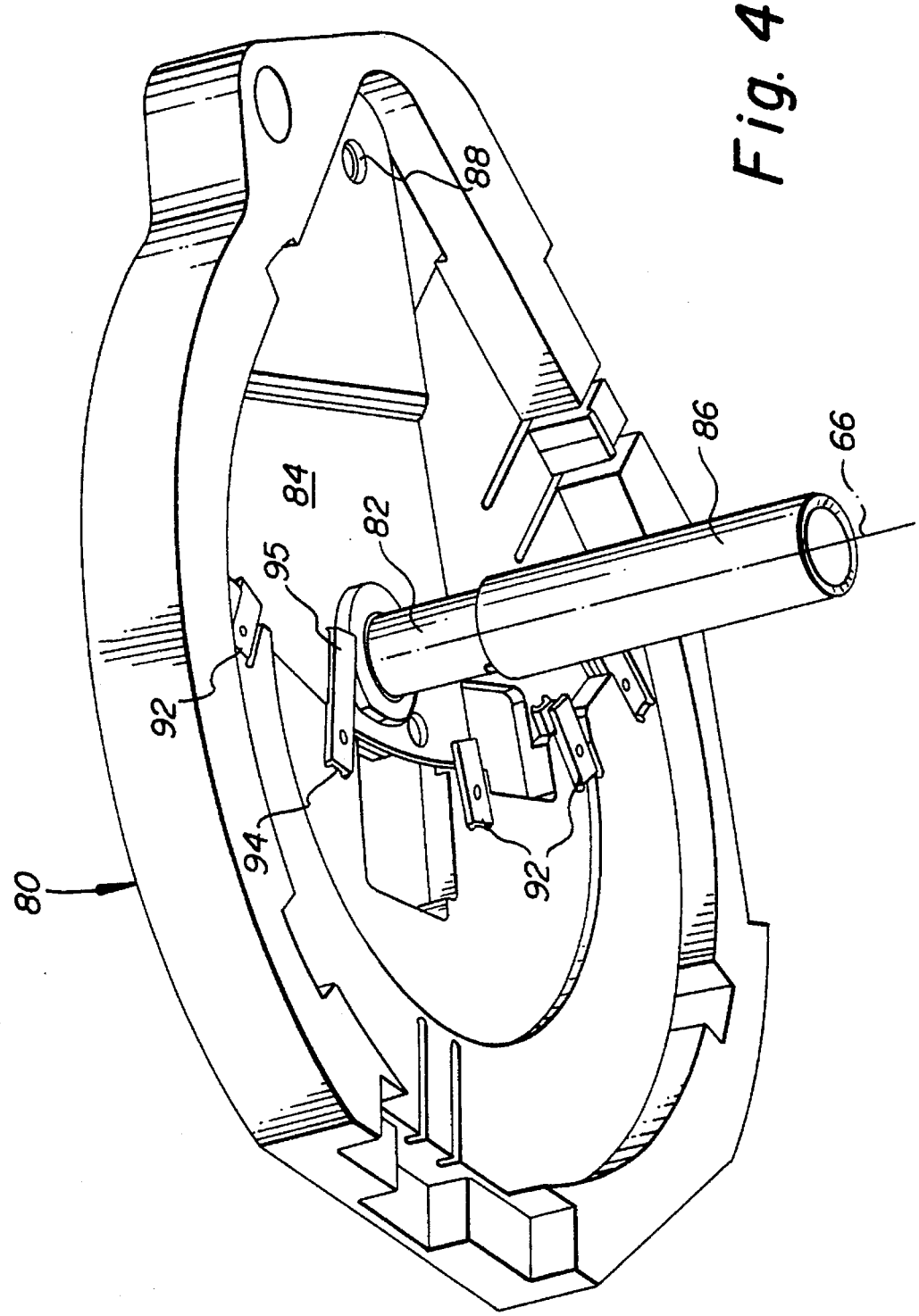
FIG. 4 is an isometric view of the underside of the cover of the invention and of the raising and pivoting mechanism of the invention.

In accordance with the invention, the mounting means of cover 80 which permits this to be accomplished comprises a connector between cover 80 and incubator 36, the connector in turn comprising, FIG. 4, a vertical shaft 82 fixed to a plate 84, the shaft being slideable through a fixed hollow tube 86 that extends from shaft 68. As described below, shaft 82 and plate 84 can only move vertically. Offset from axis 66 is a pivot aperture 88 in which a pivot pin 90, FIG. 5B, is inserted. Cover 80 is then secured to pin 90 to rotate on that pin relative to plate 84, using C-shaped guides 92 and 94 fixed to the undersurface 96 of plate 84, FIGS. 4 and 5B. The notches in Guides 92 and 94 mate with curved exterior edge 98 of plate 84. Guide 94 has camming portion 95 that provides a special function described below.

To secure shaft 86 in place and to limit shaft 82 from any but vertical motion within shaft 86, a guide pin 100, FIG. 5B, is secured in position on a stationary portion 102 of lower incubator 36, FIG. 2. Pin 100 penetrates through a through-hole 104, FIG. 5B, and rides within a slot 106, FIG. 6, cut into the side of shaft 82.

Figure 5A:
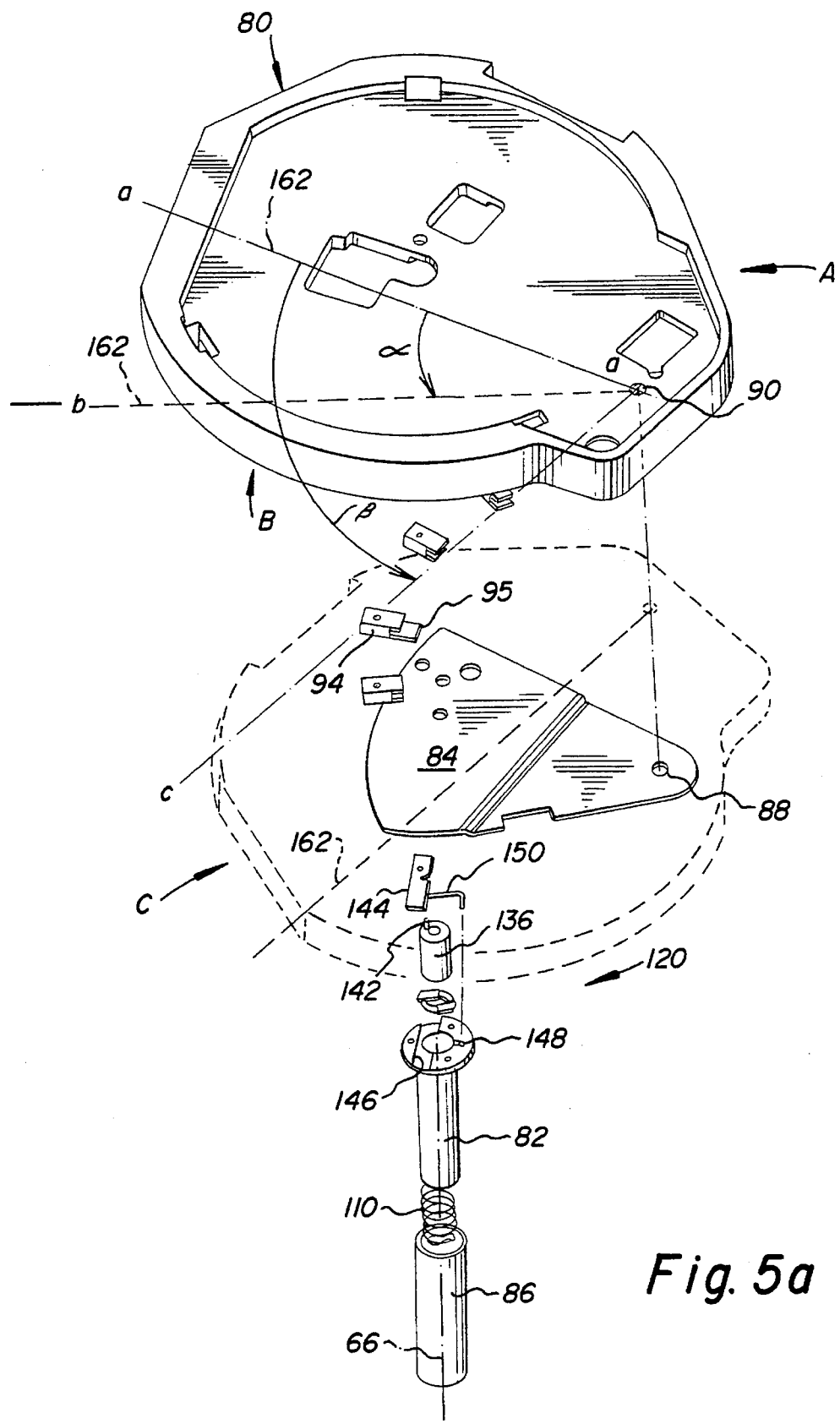
FIGS. 5A and 5B are exploded isometric views of the mechanism shown assembled in FIG. 4, FIG. 5A being from above and FIG. 5B from below (incubator 200 being removed in FIG. 5A for clarity)
Figure 5B:
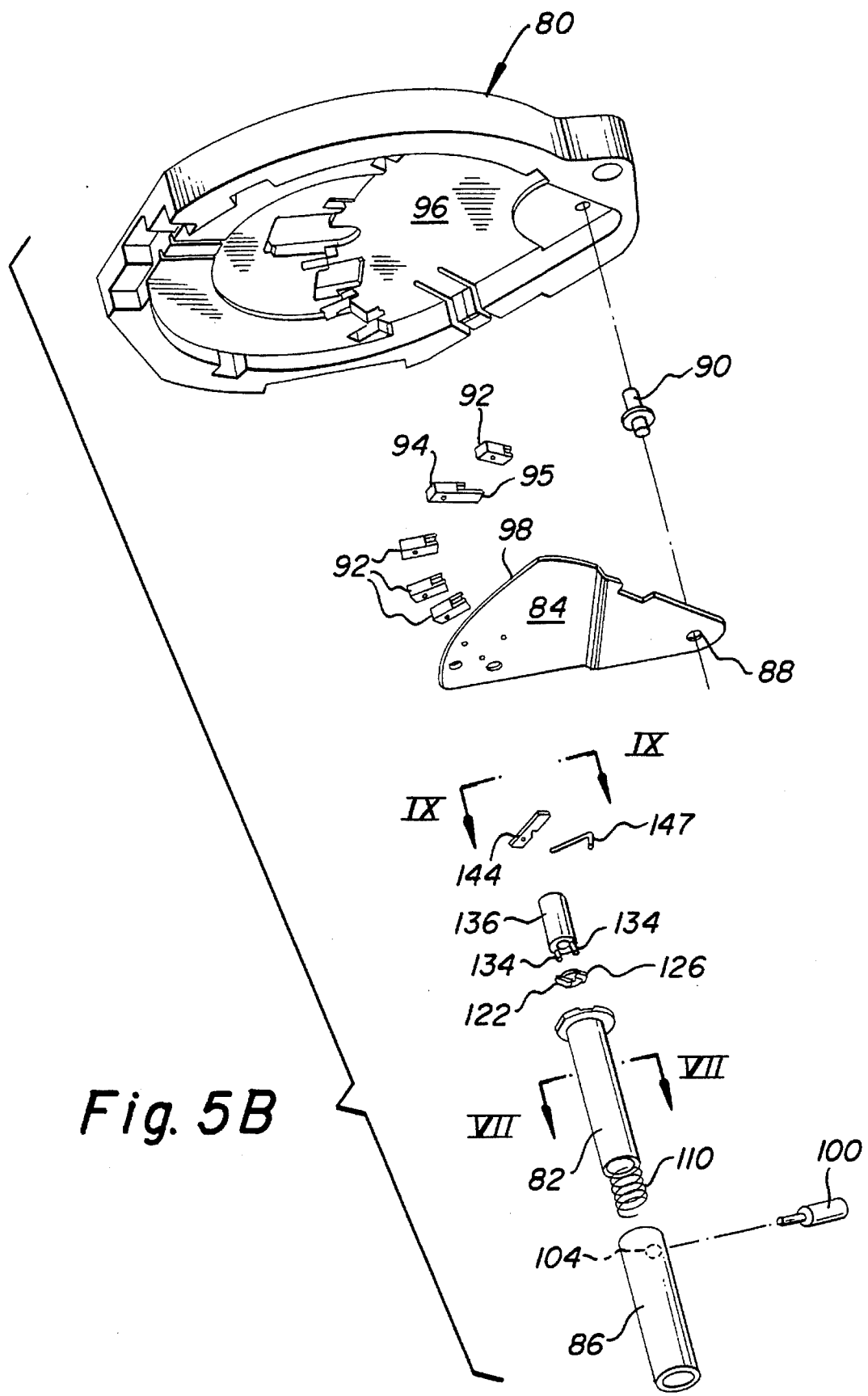

To counter some of the weight of cover 80 and the apparatus attached to it, a compression spring 110 is mounted between shaft 82 and the support of incubator 36, FIGS. 2, 5A and 5B. The spring constant is selected so that, when cover 80 is completely lowered, FIG. 2, it exerts a force about equal to the weight of cover 80 plus whatever it is carrying—in this case, the upper incubator. Thus, as cover 80 is raised as permitted by the vertical motion of plate 84 and shaft 82 relative to shaft 86, little force is required until an upper position is reached, designated the raised, superimposed position A discussed below, at which time the spring contact exerts a force that is preferably slightly less than the weight of cover 80 and its carried components.

So that the operator who is moving cover 80 to raised position A need not continue to keep it raised by lifting, a latch mechanism 120 is provided, FIG. 5A, which automatically activates once cover 80 is rotated at least an angle alpha, on pin 90, away from the position A to position B. Angle alpha is some value less than angle beta, where beta is the angle needed to place cover 80 in position C, shown in phantom, which is the raised incubator-accessible position. Most preferably, alpha is about 3° whereas beta is about 45°.

Figure 6:
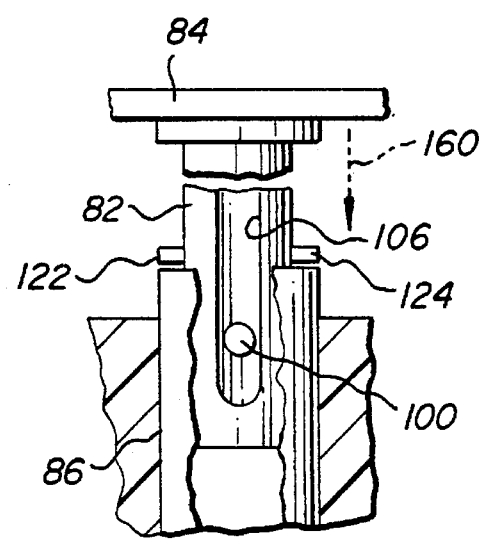
FIG. 6 is a fragmentary, elevational view, partially in section, showing shaft 86 broken away to reveal the surface details of shaft 82 inside.
Figure 7:
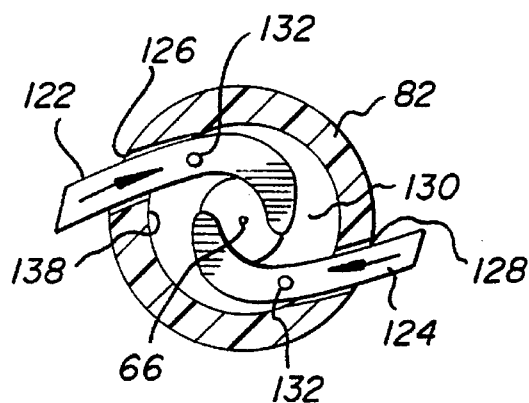
FIG. 7 is a horizontal section view taken generally horizontally through vertical shaft 82 at VII—VII in FIG. 5B, to show fingers 122 and 124.
Figure 8:
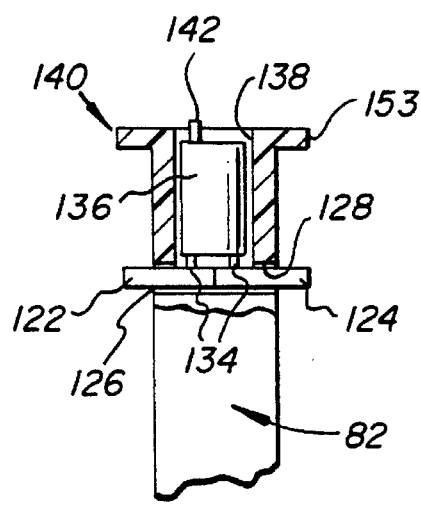
FIG. 8 is a fragmentary elevational view, partially in section, of the top portion of shaft 82 but with cam follower 144 and spring 146 removed for clarity.

Latch mechanism 120 comprises preferably two latch fingers 122, 124 mounted within shaft 82 to slide in and out of two slits 126, 128, respectively, FIG. 7. Fingers 122, 124 are supported by a ledge 130 within shaft 82, and each is driven by an aperture 132 off-center of axis 66 that mates with pins 134 mounted on a rotatable drum 136 mounted within aperture 138 at the top 140 of shaft 82, FIGS. 5B and 8. Drum 136, in turn, is rotated by reason of a pin 142 that projects upward, FIGS. 5A and 9, into engagement with a cam follower 144 that slides within a groove 146 at top 140 of shaft 82, groove 146 being off-center of axis 66. Cam follower 144 is in turn spring-biased outwardly by any suitable spring 147, FIG. 9, anchored at 148 to top 140 at one end, and engaging follower 144 at opposite end 150 so as to bias the follower outwardly, arrow 152. Such biasing causes fingers 122 and 124 to be normally biased out of shaft 82, causing the shaft, plate 84 and cover 80 to rest on the top of shaft 86, FIG. 6, with cover 80 raised to position A, FIG. 10. (Collar 153 at end 140, FIG. 9, is used to bolt plate 84 to shaft 82.)

Figure 9:
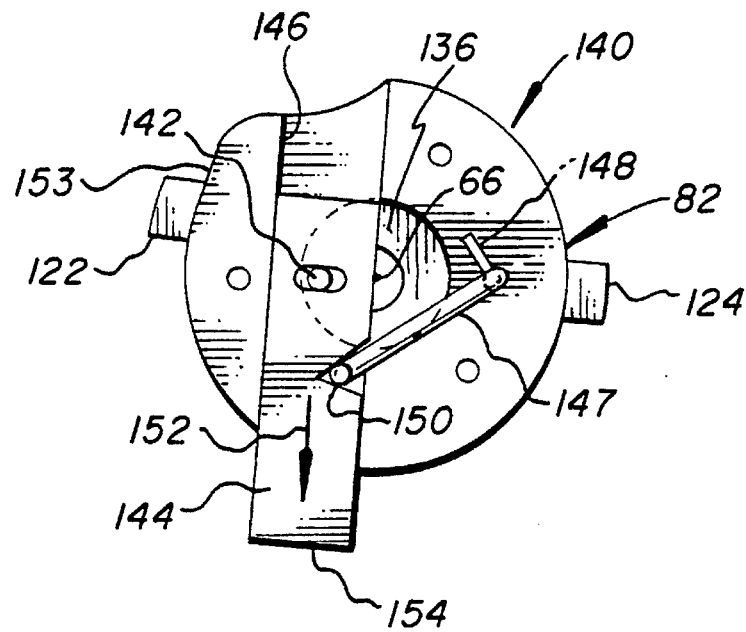
FIG. 9 is a top plan view of the assembled shaft 82 of FIG. 5B, taken generally along the line IX—IX.

However, when end 154 of follower 144, FIG. 9, is pushed inwardly against the action of spring 147 (opposite to arrow 152), drum 136 reverses its. rotation and fingers 122, 124 are pulled into shaft 82 so that shaft 82 and all it carries can be lowered, arrow 160, FIG. 6, relative to shaft 86. This is achieved when camming portion 95 that projects out from guide 94 on the undersurface 96 of cover 80, FIG. 5B, swings into contact with cam follower 144 as cover 80 is pivoted back through angle alpha, FIG. 5A, that is, from the position b-a of center line 162 of cover 80 (position B of cover 80), to position a—a. Camming portion 95 remains in contact with follower 144 when the centerline 162 is at a—a, so that fingers 122 and 124 remain withdrawn when cover 80 is at position A. In this manner, cover 80 and all that it carries can be lowered into position to once more completely cover incubator 36, FIG. 2. However, when cover 80 is at position C with centerline 162 at position c-a, incubator 36 is accessible.

To hold cover 80 down during usage of the incubators, a threaded knob, not shown, is screwed through cover 80 into the lower incubator 36. Any conventional hold-down knob can be used.

As noted, a preferred construction is one in which cover 80 carries a second incubator 200, FIG. 2, which is preferably dedicated to potentiometric-type slide test elements such as those available from Eastman Kodak Company under the trademark "Ektachem". A preferred construction of such an incubator is that disclosed and claimed in commonly-owned U.S. Ser. No. 056,637 filed on May 3, 1993 by James Miller and entitled "Improved Cap Raising Mechanism for an Incubator", now U.S. Pat. No. 5,340,540. More specifically, FIGS. 2 and 11, such an incubator comprises a heated rotor 202 having stations 204 spaced around the rotor periphery, each which receives a potentiometric slide element E', FIG. 2, covered by an evaporation cap 208 having legs 210, 212, 214, FIG. 11, that project through the rotor (omitted in FIG. 11) to a stationary cam track 220 underneath, FIG. 11. Track 220 has a plurality of rails 222, 224 and 226 each designed to act on one of the three legs 210, 212 and 214 so that cap 208 raises and lowers uniformly, without any significant sideways thrust (arrow 230 is a force less than 1G) caused by one side 232 or the other side 234 of cap 208 coming down before the other. That is, the raised portion of rail 226 is offset from the raised portions of rails 222 and 224 exactly the distance between leg 212 and leg 214. As rotor 202 is rotated, arrow 240, cap 208 thus goes up to allow a slide element E' to be inserted, arrow 242, into a station 204, and then down to cover the liquid-bearing part, without a sideways jarring of the element. (Rotation of rotor 202 is achieved by conventional means, such as a motor 290 driving a pinion gear 292, FIG. 2, the rotor rotating about an axis that is preferably horizontally displaced from axis 66, using three bearing surfaces (not shown).)

Elements E' can be loaded onto rotor 202 by the same slide insert means 50 as is used for incubator 36, or by a slide distributor such as distributor 30, FIG. 1. Because the method of loading the slide elements is not part of this invention, further description is not warranted.

Such element E' can be read by a potentiometer, not shown, coming down onto portion 300, FIG. 2, of an element E' stopped adjacent to the potentiometer.

A top cover, not shown, is preferably closed over rotor 202 and evaporation caps 208, for incubator 200.

Alternatively, it will be appreciated that cover 80 can carry instead any other piece of equipment of analyzer 12 that is conveniently located near incubator 36.

Method of Use

Figure 10:
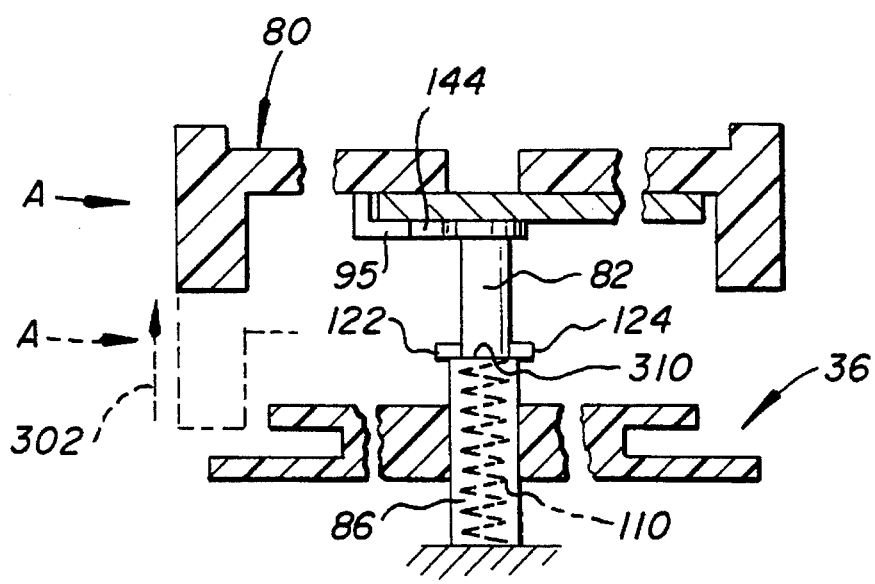
FIG. 10 is a fragmentary elevational view similar to that of FIG. 2, but showing cover 80 in its raised, superimposed position instead of its lowered position.
Figure 12A:
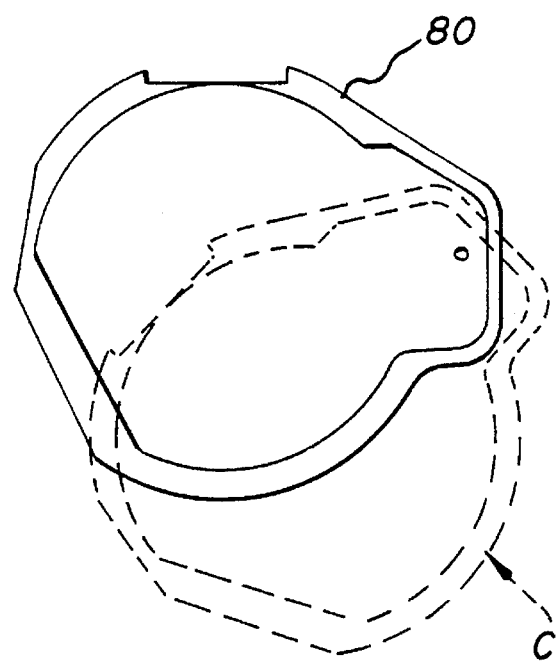
FIGS. 12A and 12B are partially schematic plan views showing the operation of the invention.
Figure 12B:
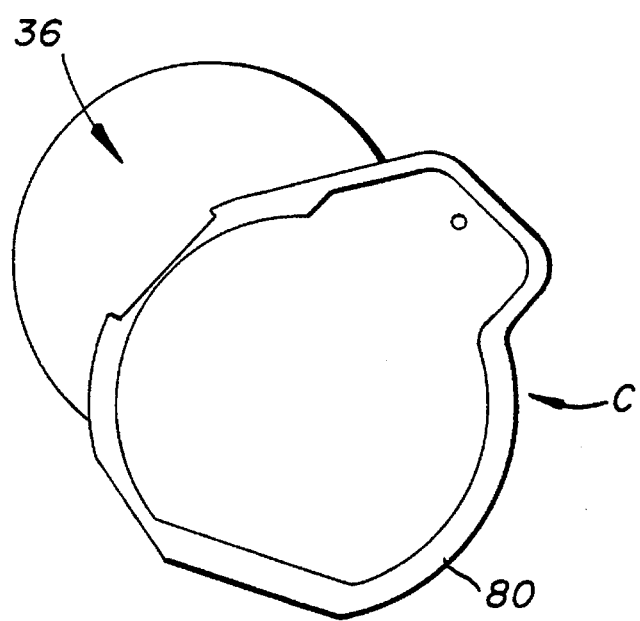

The operation of the invention will be readily apparent from the previous description.. Referring especially to FIGS. 10 and 12, when access is needed to incubator 36, the operator lifts up on cover 80 from its phantom position, FIG. 10, in the direction of arrow 302, until it reaches position A which is the raised but not pivoted, superimposed position, also shown in solid lines in FIG. 12A. Upward movement is limited by the interaction of pin 100 with the bottom of slot 106, FIG. 6. The operator then (or simultaneously with the raising along arrow 302, FIG. 10) pivots the cover until fingers 122, 124 clear the top 310 of shaft 86 and are released by cam portion 95 releasing cam follower 144. At this point fingers 122, 124 are effective in holding up cover 80 against inadvertent movement back to the covering position over incubator 36 (also resisted by spring 110.) Continued rotational movement of cover 80 allows the operator to place it in position C, shown in phantom in FIG. 12A and in solid, FIG. 12B, which is the incubator accessible position in which incubator 36 is accessible below. When access is no longer needed, the process is simply reversed. (The topmost details of the 2 incubators, though normally apparent in the views of FIGS. 12A and 12B, have been omitted for clarity.)

Although remaining incubators of analyzer 12, FIG. 1, can be used in any fashion, the stacked incubators herein described make it possible to have incubator 24 be dedicated to colorimetric end-point assays, and incubator 22 to so-called conventional rate assays such as for ALT and AST.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In an incubator useful in a clinical analyzer, the incubator comprising a rotor having stations thereon for receiving a plurality of test elements, means for rotating said rotor about an axis, a cover for said incubator, and mounting means permitting movement of said cover from a covering position to an access position moved away from said incubator to allow operator access to said incubator, the improvement wherein said mounting means comprise a connector on which said cover is mounted, between said cover and said incubator, constructed to permit said cover to be raised from and lowered to said covering position to a raised, superimposed position, but not to be pivoted, a pivot pin on said connector for pivoting said cover within a horizontal plane from said raised, superimposed position to a raised, incubator-accessible position, and back, and latch means on said connector for automatically latching said cover in said raised position as soon as said cover is pivoted in said plane a predetermined angle away from said superimposed position.

2. In an incubator useful in a clinical analyzer, the incubator comprising a rotor having stations thereon for receiving a plurality of test elements, means for rotating said rotor about an axis, a cover for said incubator, and mounting means permitting movement of said cover from a covering position to an accessible position moved away from said incubator to allow operator access to said incubator, the improvement wherein said mounting means comprise a vertical shaft penetrating to said cover through, and slidable within, said incubator, a plate on said shaft for relative vertical movement only, to and from a raised, superimposed position, a cover housing pivotally mounted within a horizontal plane on said plate to rotate from a superimposed position to an incubator accessible position, a latch for latching said cover and said plate in a raised position, and means for automatically activated said latch when said housing is rotated in said plane a predetermined angle away from said superimposed position.

3. An incubator as defined in claim 1 or 2, wherein said latch further includes a cam for automatically unlatching said cover from said raised position when said cover is pivoted less than said predetermined angle.

4. An incubator as defined in claim 3, wherein said predetermined angle is about 3 degrees.

5. An incubator as defined in claim 1 or 2, wherein said cover further comprises a second incubator.

6. An incubator as defined in claim 1, wherein said connector is generally aligned with said axis of said incubator and said pivot pin is displaced from said axis.

7. In an incubator useful in a clinical analyzer, the incubator comprising a rotor having stations thereon for receiving a plurality of test elements, means for rotating said rotor about an axis, a cover for said incubator that covers all of said stations and optionally carries analytical components, and mounting means permitting movement of said cover from a covering position over all of said stations to an access position moved away from said incubator to allow operator access to at least most of said stations in said incubator, the improvement wherein said mounting means comprise a latch, and means for automatically engaging and disengaging said latch when said cover is moved at least part way out of said covering position, said latch being disposed when engaged to keep said cover from returning to said covering position, and further including a spring mounted between said cover and said incubator, said spring having a spring constant sufficient to exert a force about equal to the weight of said cover and its carried components at said covering position and less than the weight of said cover and its carried components at the position of the engagement of said cover by said latch to counter the weight of said cover and its carried components as it is moved from or onto said incubator.

* * * * *